(12) United States Patent
Rivers et al.

(10) Patent No.: US 9,050,126 B2
(45) Date of Patent: Jun. 9, 2015

(54) ROTATIONAL ATHERECTOMY DEVICE WITH ELECTRIC MOTOR

(75) Inventors: Jody Lee Rivers, Elk River, MN (US); Charles A. Plowe, Hugo, MN (US); Cassandra Ann Piippo Svendsen, Hugo, MN (US); Walter John Dobrovolny, St. Paul, MN (US); Michael John Eng, Shoreview, MN (US); Scott M. Hanson, Savage, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 18 days.

(21) Appl. No.: 12/713,558

(22) Filed: Feb. 26, 2010

(65) Prior Publication Data
US 2011/0213391 A1 Sep. 1, 2011

(51) Int. Cl.
*A61B 17/22* (2006.01)
*A61B 17/3207* (2006.01)
(Continued)

(52) U.S. Cl.
CPC .......... *A61B 17/320758* (2013.01); *A61B 2017/00075* (2013.01); *A61B 2017/00199* (2013.01); *A61B 2017/320004* (2013.01); *A61B 2017/320766* (2013.01); *A61B 2019/466* (2013.01)

(58) Field of Classification Search
CPC .......... A61B 17/320758; A61B 2019/466; A61B 2017/00199; A61B 2017/00075; A61B 2017/320766; A61B 2017/320004
USPC ......... 606/159, 200, 180, 170, 171, 110, 127; 604/22, 508; 408/5, 7, 12, 14, 15
See application file for complete search history.

(56) References Cited

U.S. PATENT DOCUMENTS

| 3,374,425 | A | | 3/1968 | Barditch et al. | |
|---|---|---|---|---|---|
| 4,304,511 | A | * | 12/1981 | Machida | 408/11 |

(Continued)

FOREIGN PATENT DOCUMENTS

| DE | 4334266 | 4/1994 |
|---|---|---|
| JP | 7-509117 | 10/1995 |

(Continued)

OTHER PUBLICATIONS

International Search Report from related PCT/US2010/058286 application.

*Primary Examiner* — Ryan Severson
*Assistant Examiner* — Anh Dang
(74) *Attorney, Agent, or Firm* — Winthrop & Weinstine, P.A.

(57) ABSTRACT

An atherectomy device is disclosed, which is rotationally driven by an electric motor. In some designs, the device includes features unavailable on gas turbine-driven systems, such as the storing in memory of low/medium/high preset rotation speeds for particular models of handle, calculations of the amount of saline left in the IV and associated warnings when it gets sufficiently low, and automatic adjustment of the IV pump rate to a predetermined or calculated level when the rotational speed of the motor is changed. The electric motor has far more rotational inertia than a comparable gas turbine, so the system includes a control mechanism that helps prevent damage from excessive torque being applied to the distal end of the drive shaft. When an obstruction at the distal end is detected, by a drop in the motor rotational speed, the motor is released and is allowed to spin freely as a flywheel. The freely-spinning motor allows the large angular momentum of the system to dissipate rapidly and safely, without excessive torque to the drive shaft.

10 Claims, 9 Drawing Sheets

(51) Int. Cl.
*A61B 17/00* (2006.01)
*A61B 17/32* (2006.01)
*A61B 19/00* (2006.01)

(56) References Cited

U.S. PATENT DOCUMENTS

| | | | |
|---|---|---|---|
| 4,979,951 A | 12/1990 | Simpson |
| 5,026,384 A | 6/1991 | Farr et al. |
| 5,078,723 A | 1/1992 | Dance et al. |
| 5,100,425 A | 3/1992 | Fischell et al. |
| 5,158,564 A | 10/1992 | Schnepp-Pesch et al. |
| 5,217,478 A | 6/1993 | Rexroth |
| 5,261,877 A | 11/1993 | Fine et al. |
| 5,336,167 A | 8/1994 | Sullivan et al. |
| 5,358,509 A | 10/1994 | Fine et al. |
| 5,370,651 A | 12/1994 | Summers |
| 5,423,740 A | 6/1995 | Sullivan et al. |
| 5,431,673 A | 7/1995 | Summers et al. |
| 5,490,859 A | 2/1996 | Mische et al. |
| 5,501,694 A | 3/1996 | Ressemann et al. |
| 5,540,681 A | 7/1996 | Strul et al. |
| 5,540,707 A | 7/1996 | Ressemann et al. |
| 5,556,198 A | 9/1996 | Dickson, Jr. et al. |
| 5,627,710 A | 5/1997 | Schoeffler |
| 5,630,823 A | 5/1997 | Schmitz-Rode et al. |
| 5,746,758 A | 5/1998 | Nordgren et al. |
| 5,792,157 A | 8/1998 | Mische et al. |
| 5,836,868 A | 11/1998 | Ressemann et al. |
| 5,921,956 A | 7/1999 | Grinberg et al. |
| 5,938,672 A | 8/1999 | Nash |
| 6,398,755 B1 | 6/2002 | Belef et al. |
| 6,447,443 B1 | 9/2002 | Keogh et al. |
| 6,454,717 B1* | 9/2002 | Pantages et al. .............. 600/466 |
| 6,494,890 B1 | 12/2002 | Shturman et al. |
| 6,503,261 B1 | 1/2003 | Bruneau et al. |
| 6,565,588 B1 | 5/2003 | Clement et al. |
| 6,758,818 B2 | 7/2004 | Pantages et al. |
| 6,818,001 B2 | 11/2004 | Wulfman et al. |
| 6,936,056 B2 | 8/2005 | Nash et al. |
| 6,958,071 B2 | 10/2005 | Carusillo et al. |
| 7,344,546 B2 | 3/2008 | Wulfman et al. |
| 2002/0007190 A1 | 1/2002 | Wulfman et al. |
| 2002/0058956 A1 | 5/2002 | Honeycutt et al. |
| 2002/0151799 A1 | 10/2002 | Pantages et al. |
| 2003/0125717 A1 | 7/2003 | Whitman |
| 2004/0097995 A1 | 5/2004 | Nash et al. |
| 2004/0220519 A1 | 11/2004 | Wulfman et al. |
| 2004/0243162 A1 | 12/2004 | Wulfman et al. |
| 2006/0020282 A1 | 1/2006 | Henniges et al. |
| 2006/0184186 A1 | 8/2006 | Noone |
| 2007/0225739 A1 | 9/2007 | Pintor et al. |
| 2007/0239140 A1 | 10/2007 | Chechelski et al. |
| 2007/0239182 A1 | 10/2007 | Glines et al. |
| 2007/0270688 A1 | 11/2007 | Gelbart et al. |
| 2007/0282358 A1 | 12/2007 | Remiszewski et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0058846 A1 | 3/2008 | Vosough |
| 2008/0065125 A1 | 3/2008 | Olson |
| 2008/0097500 A1 | 4/2008 | Nash et al. |
| 2008/0103446 A1* | 5/2008 | Torrance et al. .............. 604/123 |
| 2008/0140101 A1 | 6/2008 | Carley et al. |
| 2008/0221601 A1 | 9/2008 | Huynh et al. |
| 2008/0228208 A1 | 9/2008 | Wulfman et al. |
| 2008/0269789 A1 | 10/2008 | Eli |
| 2008/0306498 A1* | 12/2008 | Thatcher et al. .............. 606/159 |
| 2010/0125276 A1* | 5/2010 | Palermo .......................... 606/80 |

FOREIGN PATENT DOCUMENTS

| | | |
|---|---|---|
| JP | 2002538927 | 11/2002 |
| JP | 2006514577 | 5/2006 |
| JP | 2008-200513 | 9/2008 |
| WO | WO00/56230 | 9/2000 |
| WO | WO2006/126076 | 11/2006 |

* cited by examiner

ROTATIONAL ATHERECTOMY DEVICE WITH ELECTRIC MOTOR

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The invention relates to devices and methods for removing tissue from body passageways, such as removal of atherosclerotic plaque from arteries, utilizing a rotational atherectomy device. In particular, the invention relates to improvements in a rotational atherectomy device having an electric motor.

2. Description of the Related Art

Atherectomy is a non-surgical procedure to open blocked coronary arteries or vein grafts by using a device on the end of a catheter to cut or shave away atherosclerotic plaque (a deposit of fat and other substances that accumulate in the lining of the artery wall). For the purposes of this application, the term "abrading" is used to describe the grinding and/or scraping action of such an atherectomy head.

Atherectomy is performed to restore the flow of oxygen-rich blood to the heart, to relieve chest pain, and to prevent heart attacks. It may be done on patients with chest pain who have not responded to other medical therapy and on certain of those who are candidates for balloon angioplasty (a surgical procedure in which a balloon catheter is used to flatten plaque against an artery wall) or coronary artery bypass graft surgery as well as peripheral artery treatments. It is sometimes performed to remove plaque that has built up after a coronary artery bypass graft surgery.

Atherectomy uses a rotating shaver or other device placed on the end of a catheter to slice away or destroy plaque. At the beginning of the procedure, medications to control blood pressure, dilate the coronary arteries, and prevent blood clots are administered. The patient is awake but sedated. The catheter is inserted into an artery in the groin, leg, or arm, and threaded through the blood vessels into the blocked coronary artery. The cutting head is positioned against the plaque and activated, and the plaque is ground up or suctioned out.

The types of atherectomy are rotational, directional, and transluminal extraction. Rotational atherectomy uses a high speed rotating shaver to grind up plaque. Directional atherectomy was the first type approved, but is no longer commonly used; it scrapes plaque into an opening in one side of the catheter. Transluminal extraction coronary atherectomy uses a device that cuts plaque off vessel walls and vacuums it into a bottle. It is used to clear bypass grafts.

Performed in a cardiac catheterization lab, atherectomy is also called removal of plaque from the coronary arteries. It can be used instead of, or along with, balloon angioplasty.

Several devices have been disclosed that perform rotational atherectomy. For instance, U.S. Pat. No. 5,360,432, issued on Nov. 1, 1994 to Leonid Shturman, and titled "Abrasive drive shaft device for directional rotational atherectomy" discloses an abrasive drive shaft atherectomy device for removing stenotic tissue from an artery, and is incorporated by reference herein in its entirety. The device includes a rotational atherectomy apparatus having a flexible, elongated drive shaft having a central lumen and a segment, near its distal end, coated with an abrasive material to define an abrasive segment. At sufficiently high rotational speeds, the abrasive segment expands radially, and can sweep out an abrading diameter that is larger than its rest diameter. In this manner, the atherectomy device may remove a blockage that is larger than the catheter itself. Use of an expandable head is an improvement over atherectomy devices that use non-expandable heads; such non-expandable devices typically require removal of particular blockages in stages, with each stage using a differently-sized head.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

A typical atherectomy device includes a single-use disposable portion, which can be attached and detached from a non-disposable control unit (also referred to as a controller). The disposable portion includes elements that are exposed to saline and to the bodily fluids of the patient, such as a handle, a catheter, a rotatable drive shaft, and an abrasive head. The handle includes a turbine that rotates the drive shaft, and a knob that can longitudinally advance and retract the drive shaft along the catheter. Often, the device has a foot switch that activates the handle.

Typical atherectomy devices use pneumatic power to drive the drive shaft, with the controller managing the amount of compressed air that is delivered to the turbine in the handle. The compressed air spins the turbine that, in turn, spins the drive shaft, and spins an abrasive crown attached to the drive shaft. Orbiting motion of the crown enlarges and widens the channel opening of a restricted or blocked vascular vessel.

The pneumatic system required for such a device is substantial. For instance, a typical pneumatic system requires compressed air or nitrogen, with a minimum pressure of 100 pounds per square inch (689,000 pascals, or 6.8 atmospheres), and a minimum flow volume rate of 4 cubic feet per minute (113 liters per minute, or 1.9 liters per second). The controller for such an air system is mechanically complicated, and can be quite expensive.

Accordingly, there exists a need for an atherectomy device that maintains the functionality of current devices without requiring a substantial pneumatic system.

BRIEF SUMMARY OF THE INVENTION

An embodiment is a rotational atherectomy system, comprising: an elongated, flexible drive shaft having a distal end for insertion into a vasculature of a patient and having a proximal end opposite the distal end remaining outside the vasculature of the patient; an eccentric solid crown attached to the drive shaft proximate the distal end of the drive shaft; an electric motor rotatably coupled to the proximal end of the drive shaft, the electric motor being capable of rotating the drive shaft in a first direction and in a second direction opposite the first direction; and control electronics for monitoring and controlling the rotation of the electric motor. The drive shaft and eccentric solid crown, when rotating, have a torque limited by a current supplied to the electric motor.

Another embodiment is a rotational atherectomy system, comprising: an elongated, flexible drive shaft having a distal end for insertion into a vasculature of a patient and having a proximal end opposite the distal end remaining outside the vasculature of the patient; an eccentric solid crown attached to the drive shaft proximate the distal end of the drive shaft; an electric motor rotatably coupled to the proximal end of the drive shaft, the electric motor being capable of rotating the drive shaft in a first direction and in a second direction opposite the first direction; a handle housing the electric motor; control electronics for monitoring and controlling the rotation of the electric motor, the control electronics including an algorithm that detects and controls when the drive shaft and eccentric solid crown encounter a blockage in the vasculature that rapidly slows their rotation; and a control unit separate from the handle and electrically tethered to the handle.

Yet another embodiment is a rotational atherectomy system, comprising: an elongated, flexible drive shaft having a distal end for insertion into a vasculature of a patient and having a proximal end opposite the distal end remaining outside the vasculature of the patient; an eccentric solid crown attached to the drive shaft proximate the distal end of the drive shaft; an electric motor rotatably coupled to the proximal end of the drive shaft, the electric motor being capable of rotating the drive shaft in a first direction and in a second direction opposite the first direction; and control electronics for monitoring and controlling the rotation of the electric motor. The drive shaft and eccentric solid crown, when rotating, have a torque limited by a current supplied to the electric motor. The control electronics include an algorithm that detects and controls when the drive shaft and eccentric solid crown encounter a blockage in the vasculature that rapidly slows their rotation. The control electronics include limits on maximum and minimum rotational speeds of the electric motor. The control electronics include limits on maximum and minimum current supplied to the electric motor. The control electronics include limits on maximum and minimum torque delivered by the electric motor. The control unit includes a void detector that ensures reliable delivery of saline to the vasculature of the patient.

Still another embodiment is a rotational atherectomy system, comprising: an elongated, flexible drive shaft having a distal end for insertion into a vasculature of a patient and having a proximal end opposite the distal end remaining outside the vasculature of the patient; an abrasive element attached to the drive shaft proximate the distal end of the drive shaft; an electric motor rotatably coupled to the proximal end of the drive shaft, the electric motor being capable of rotating the drive shaft; and control electronics for monitoring and controlling the rotation of the electric motor, the control electronics including an algorithm for limiting the torque on the drive shaft when the abrasive element encounters an obstruction and ceases rotation, the algorithm comprising: detecting a decrease in the rotational speed of the electric motor; and releasing the motor, thereby allowing the motor to spin freely as a flywheel.

DETAILED DESCRIPTION OF THE INVENTION

An atherectomy device is disclosed, which is rotationally driven by an electric motor. In some designs, the device includes features unavailable on gas turbine-driven systems, such as the storing in memory of low/medium/high preset rotation speeds for particular models of handle, calculations of the amount of saline left in the IV and associated warnings when it gets sufficiently low, and automatic adjustment of the IV pump rate to a predetermined or calculated level when the rotational speed of the motor is changed. The electric motor has far more rotational inertia than a comparable gas turbine, so the system includes a control mechanism that helps prevent damage from excessive torque being applied to the distal end of the drive shaft. When an obstruction at the distal end is detected, by a drop in the motor rotational speed, the motor is released and is allowed to spin freely as a flywheel. The freely-spinning motor allows the large angular momentum of the system to dissipate rapidly and safely, without excessive torque to the drive shaft.

A less complex atherectomy device is also disclosed, which lacks several of the more sophisticated control features mentioned above. This simpler device may includes an electric motor with on-board firmware, a motor driver and a reusable saline pump, but may lack sophisticated software control. Such a device may cost less to manufacture, and may be sold as a lower-cost alternative to the device having more sophisticated controls.

The preceding paragraphs are merely a summary, and should not be construed as limiting in any way. A more detailed description follows.

Figure 1:
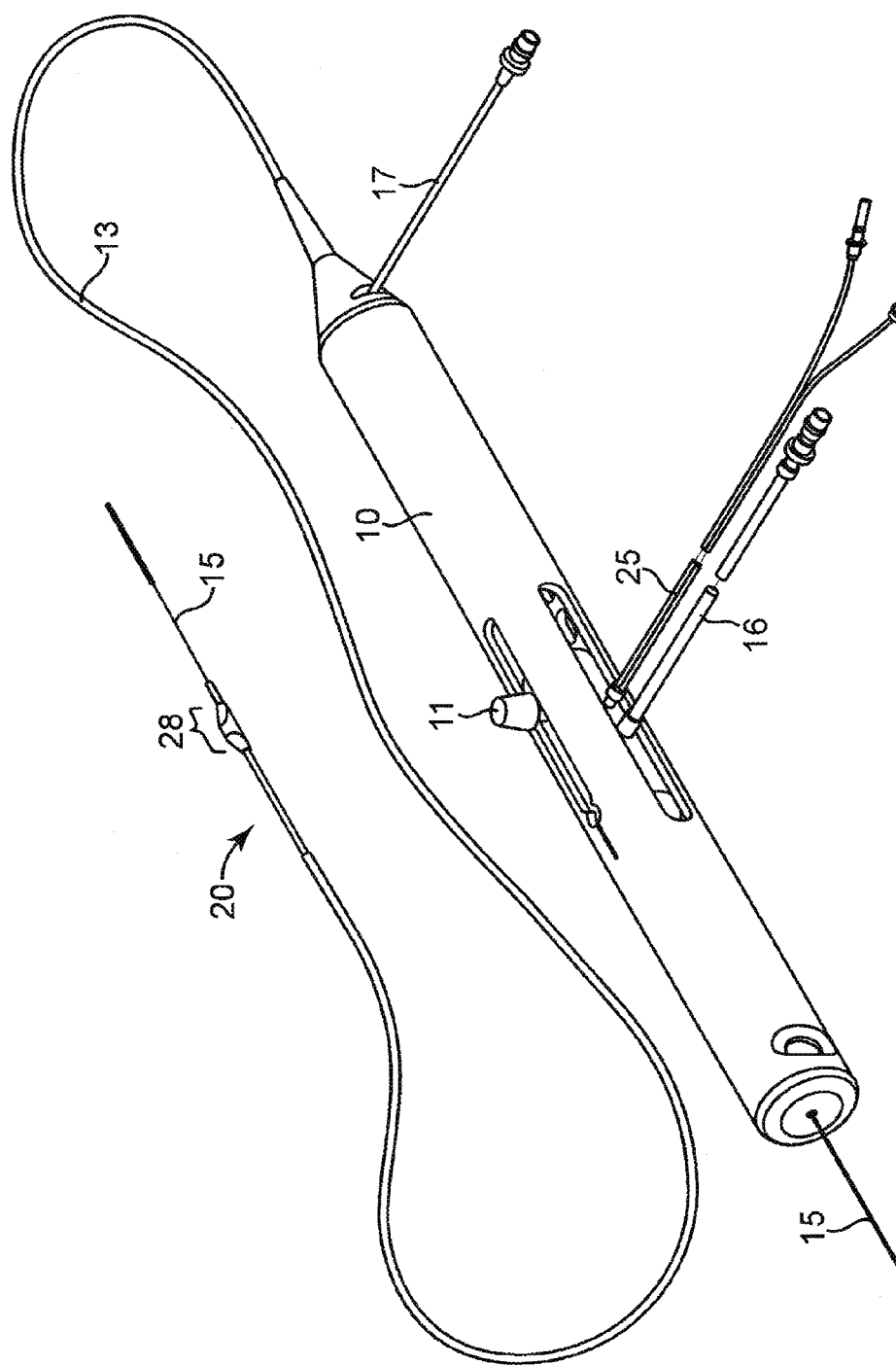
FIG. 1 is a perspective view of a known rotational atherectomy device.

FIG. 1 is a schematic drawing of a typical known rotational atherectomy device. The device includes a handle portion 10, an elongated, flexible drive shaft 20 having an eccentric enlarged abrading head 28, and an elongated catheter 13 extending distally from the handle portion 10. The drive shaft 20 is constructed from helically coiled wire as is known in the art and the abrading head 28 is fixedly attached thereto. The catheter 13 has a lumen in which most of the length of the drive shaft 20 is disposed, except for the enlarged abrading head 28 and a short section distal to the enlarged abrading head 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20 (details regarding such handles and associated instrumentation are well know in the industry, and are described, e.g., in U.S. Pat. No. 5,314,407, issued to Auth, and incorporated by references herein in its entirety). The handle 10 also desirably includes a control knob 11 for advancing and retracting the turbine and drive shaft 20 with respect to the catheter 13 and the body of the handle.

The abrasive element 28 in FIG. 1 is an eccentric solid crown, attached to the drive shaft 20 near the distal end of the drive shaft 20. The term "eccentric" is used herein to denote that the center of mass of the crown is laterally displaced away from the rotational axis of the drive shaft 20. As the drive shaft rotates rapidly, the displaced center of mass of the crown causes the drive shaft to flex radially outward in the vicinity of the crown as it spins, so that the crown may abrade over a larger diameter than its own rest diameter. Eccentric solid crowns are disclosed in detail in, for example, U.S. patent application Ser. No. 11/761,128, filed on Jun. 11, 2007 to Thatcher et al. under the title, "Eccentric abrading head for high-speed rotational atherectomy devices", published on Dec. 11, 2008 as U.S. Patent Application Publication No. US2008/0306498, and incorporated by reference herein in its entirety.

The present application is directed mainly to an electric motor in the handle, which may improve upon the air- or nitrogen-fed turbine of FIG. 1. In this respect, many or all of the other elements of the known atherectomy device of FIG. 1 may be used with the present disclosed head design, including the catheter 13, the guide wire 15, the control knob 11 on the handle 10, the helically coiled drive shaft 20 and the eccentric solid crown 28.

There are many combinations of features that may be included with the electrical device. Two such cases are described in the figures and text that follow. The first case has relatively few features, and the second case has many more features. Each has its advantages. For instance, a device having relatively few features may be less expensive to produce than a relatively feature-laden device, and may be sold and marketed as such. Likewise, a device having a lot of features may be sold and marketed as a high-performance device, which may command a higher price than the relatively feature-free device. Both are described in detail below, beginning with the device having relatively few features.

Figure 12:
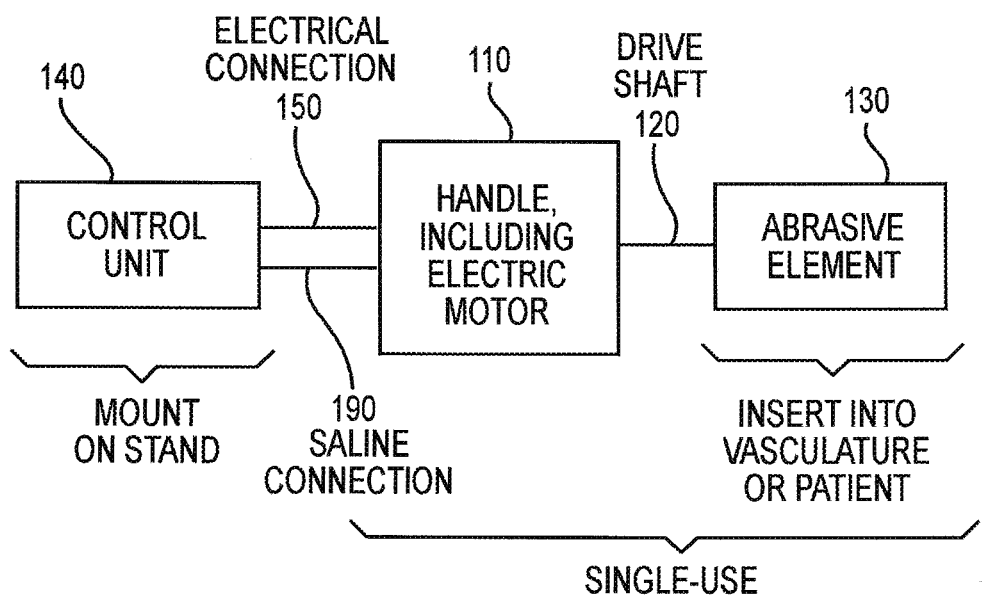
FIG. 12 shows a block diagram of an atherectomy device having an electric motor.

FIG. 12 is a block diagram of an atherectomy device having an electric motor and relatively few features.

A control unit 140 is the non-disposable portion of the device, which may be reused from procedure to procedure. The control unit may be mounted on a stand, as noted in FIG. 12, or may function as a stand-alone device that may be placed on a countertop.

The control unit 140 has an electrical connection 150 with the handle 110. In many cases, the control unit 140 functions as a power supply for the motor in the handle 110, and the electrical connection 150 is no more than the two conductive elements required for current flow (or, optionally, three, if a separate ground is used). Typically, the control unit 140 supplies a controllable and variable DC voltage to the handle 110, with the voltage varying in an open-loop fashion to control the rotational speed of the motor in the handle 110. Note that an AC voltage may also be used. For this simple electrical connection 150, no communication is possible between the handle 110 and the control unit 140; the control unit 140 simply powers the motor in the handle 110. Note that in other cases, the electrical connection 150 may be more sophisticated and may include one- or two-way communication between the control unit 140 and the handle 110; such a case is described below for the relatively feature-laden device.

The control unit 140 also includes a reusable saline pump. Such a pump directs saline at a predetermined rate from a bag, or other suitable source, through a saline connection 190, into the handle 110. Suitable plumbing inside the handle 110 directs the saline into the catheter, where it fills the space surrounding the drive shaft and serves to lubricate and clean the system. At a minimum, the control unit 140 needs to regulate the rate at which saline is pumped into the handle, and needs to inform the operator of the status of the pump. These two functions are described below.

At a minimum, the saline pump uses two pump rates, which are commonly designated as "low" and "high". Typically, the low and high speeds are hard-coded in the firmware of the control unit 140. Alternatively, more than two discrete pump rates may be used, and/or a continuously varying pump rate may be used. Typically, the low pump rate is used to flush the system, at the beginning of the procedure before the drive shaft begins its rapid rotation. The high pump rate is typically used during the procedure, when the drive shaft is rotating rapidly. In some cases, the pump rate is varied between high and low automatically, depending on the control unit power supply setting and/or the desired rotational speed of the motor in the handle. In some cases, at the beginning of each procedure, the user is instructed to turn the pump on at a low flow rate, to wait for a particular time, and to then turn the flow rate up to high.

The device may use a weight sensor to monitor the level of the saline. Such a weight sensor may be a spring-like device from which a saline bag is hung. If the hung weight of the bag and its contents drops below a predetermined threshold, a switch in the weight sensor is triggered. The saline typically arrives in a standard-sized bag, such as 200 milliliters, although any bag size may also be used. A weight sensor may also be used on a platform-like device, on which the saline bag may be placed. If the weight of the bag drops below a predetermined level, then the pump is turned off, the motor is powered down (to prevent damage to the device and to the patient that might occur from running the device without saline), and the operator is notified.

The operator is notified of the pump system status through the control unit. One simple notification system is described in detail below, although any suitable notification system may be used.

In this simple notification system, the status is provided by three differently-colored light emitting diodes (LEDs). A "green" light may indicate that the pump is operating normally and that the handle is powered properly. There is an internal circuit that monitors the 48-volt power supply for the handle. A "yellow" light may indicate that something is not right with the system; a door may be open, or there may be some other correctable problem with the system. A "red" light may indicate that the bag has run out of saline. It will be understood that other indication systems may be used as well.

The control unit 140 typically includes a cumulative time monitor, which ensures that the total operational time of the device does not exceed a predetermined threshold, such as nine minutes. Other predetermined time thresholds may be used, as well. The control unit 140 typically emits a warning and/or disables the motor once the cumulative operation time has been reached.

In some alternative designs, the electric motor is included within the control unit 140, rather than in the handle 110, and the electric connection 150 is replaced by a mechanical connection to transfer the rotation of the motor to the drive shaft.

The remainder of this document describes the relatively feature-laden device, which includes most or all of the functionality of the device of FIG. 12, in addition to many features not present in the device of FIG. 12.

Figure 2:
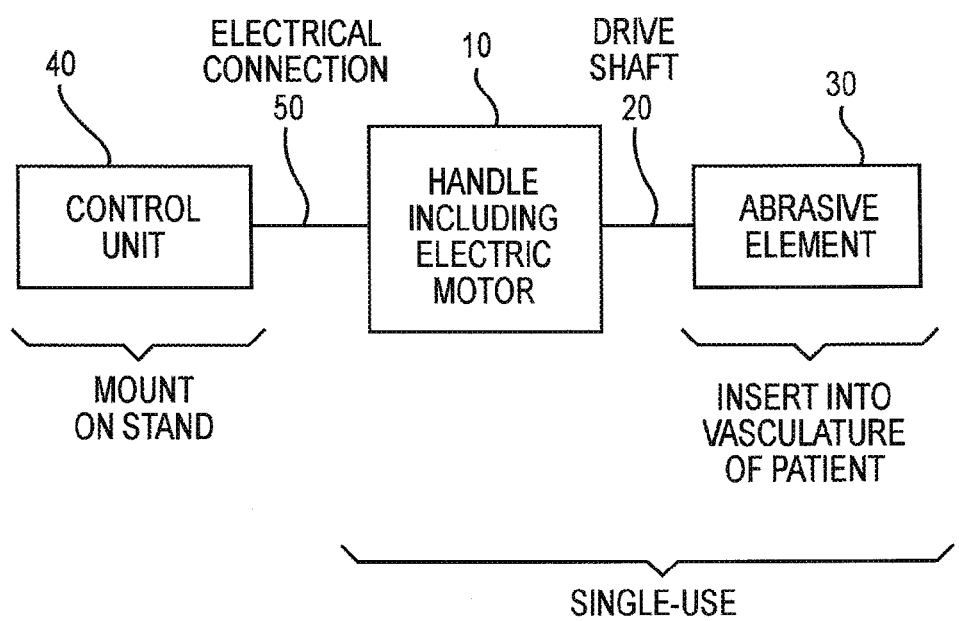
FIG. 2 shows a block diagram of an atherectomy device having an electric motor.

To start, FIG. 2 shows a block diagram of the atherectomy device having an electric motor.

A control unit 40 (also referred to as a controller) is the non-disposable portion of the device, and includes most of the electrical functions of the device that aren't directly related to driving the motor. For instance, the control unit 40 can recognize which type of handle is plugged into it, includes controls for setting the desired speed of the motor, and includes controls for the pump that delivers saline down the catheter.

The control unit 40 has an electrical connection 50 to the handle 10. In addition to having the control knob and the associated mechanical structure that can advance and retract the abrasive element with respect to the catheter, the handle 10 includes the actual electric motor and the mechanical coupling of the motor to the drive shaft 20.

The drive shaft 20 extends from the mechanical coupling with the motor, located in the handle 10, through the catheter to within the vasculature of the patient. The proximal (near) end of the drive shaft 20 is within the handle 10, and the distal (far) end of the drive shaft 20 extends to the blockage within the blood vessel. An abrasive element 30 is attached to, or made integral with, the drive shaft 20, and is located at or near the distal end of the drive shaft.

The handle 10, the catheter, and the drive shaft 20 are all designed for single use, and are typically disposed of once the procedure is completed. The control unit 40 is retained by the practitioner for future repeated uses.

As an alternative, the electric motor itself may be located within the control unit 40, rather than in the single-use handle 10. Locating the motor in the control unit 40 would require an additional mechanical coupling between the control unit 40 and the handle 50. The handle would still include the control knob 11 that advances and retracts the abrasive element within the catheter.

Figure 3:
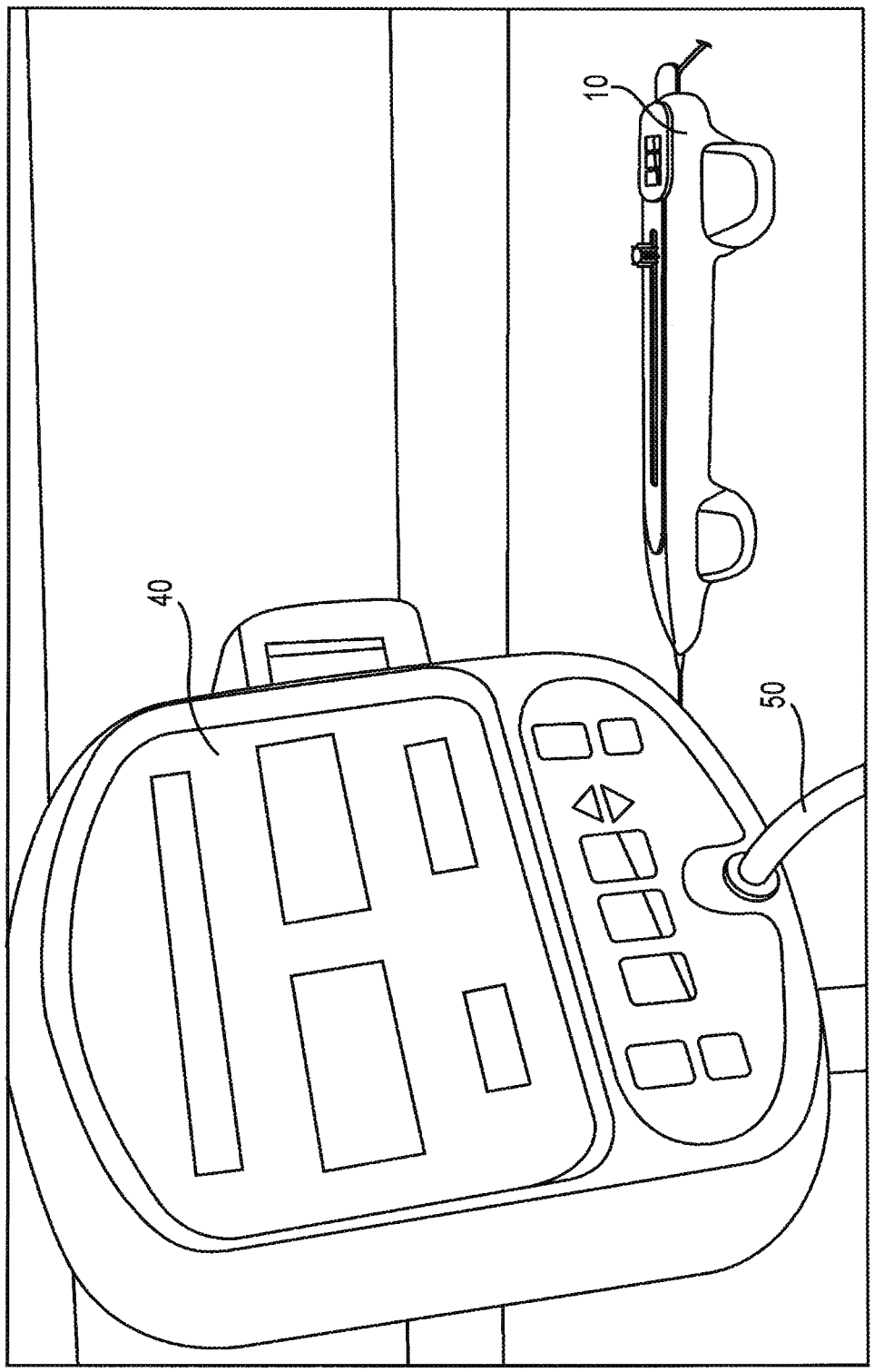
FIG. 3 is a plan drawing of an exemplary control unit and handle.

FIG. 3 is a plan drawing of an exemplary control unit 40 and handle 10. In this example, the electrical connection 50 comes out the front of the control unit 40 and enters the handle 10 on its right side, in the view of FIG. 3. The catheter and drive shaft attach to the left side of the handle 10, and are not shown explicitly in the view of FIG. 3.

Many of the various device features are described below, and for convenience are done so with respect to their corresponding controls on the control unit 40. It will be understood that any suitable controls, with any suitable layout on the control unit 40, may be used for the described functions, and that the controls shown in the figures are merely examples.

Figure 4:
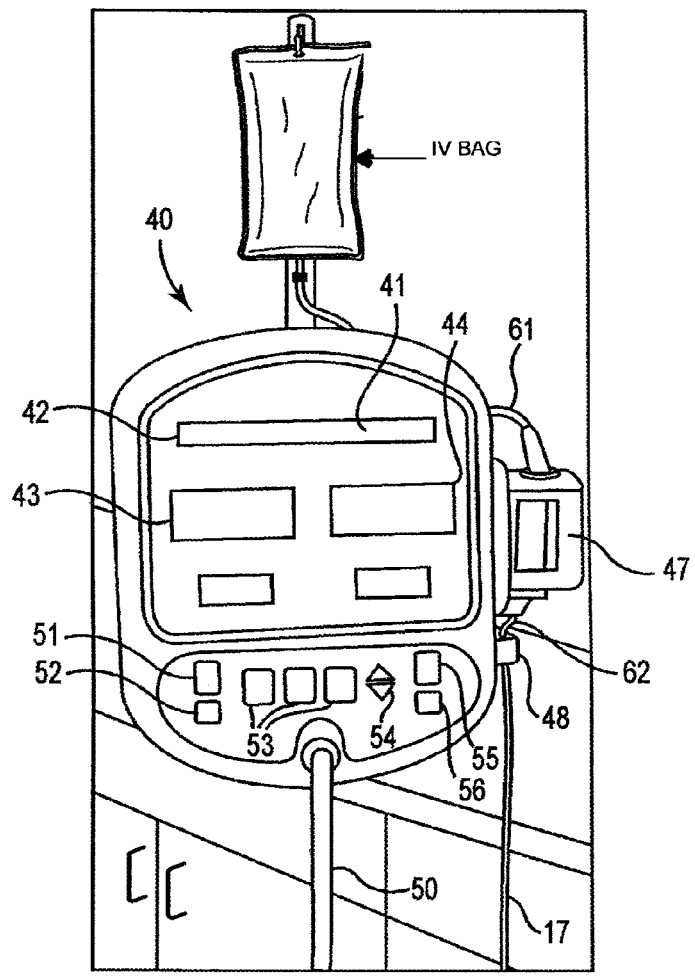
FIG. 4 is a front-view drawing of the control unit.

FIG. 4 is a front-view drawing of the control unit 40. The rear of the control unit may be placed on a counter top, clamped to a stand, hung from a pole, or may have another suitable mount. In some cases, the control unit is supported by an IV pole, so that an IV saline may be hung from higher up on the same pole and may feed a pump on the control unit 40.

Starting from the top down, the topmost element is a notification screen 41, which can display text and character messages. For instance, the screen 41 may display the status of various components, such as "saline pump off". As another example, when a particular handle is plugged in, the controller unit 40 recognizes it and may display its name and relevant information on the notification screen 41. As another example, the notification screen 41 may also display error and troubleshooting information for the practitioner.

The running speed 42 is the actual rotational velocity of the proximal end of the drive shaft, in units of 1,000 RPM (revolutions per minute), or kRPM. The running speed 42 is typically updated several times per second, and in some cases may be displayed in relatively large LEDs that are readily visible to the practitioner. Rotational speeds of up to 200 kRPM are typical.

The rotational speed may be obtained from the electric motor itself. For instance, the motor may include one or more Hall effect sensors that produce an electrical signal each time the motor rotates past a particular point. The rotational speed is proportional to the rate of the signals, or, equivalently, is inversely proportional to the time intervals between the electrical signals. Alternatively, any suitable sensors and signals may be used.

Below the actual running speed 42 is the selected speed 43, also displayed in kRPM. During operation, a control circuit (feedback loop) in the control unit 40 and/or the handle 10 adjusts the motor current and/or voltage to keep the actual running speed 42 as close as possible to the selected speed 43.

The event time 44 is the elapsed time for a particular run of the device. The event time 44 typically displays in minutes:seconds, although any suitable unit may be used.

Below the event time 44 is the total time 45, which is the cumulative total time 45 that the particular device has been operated. The motivation for such a measurement may be explained as follows.

It is typical for the atherectomy device to be rated only for a particular time, such as nine minutes, beyond which use is not recommended. In other words, a device may be repeatedly turned off and on during the course of a full procedure. Such switching off and on is permissible as long as the total cumulative time during which the device is actually on does not exceed a particular value, such as nine minutes. Typically, the handle 10 includes electronics that store the cumulative on-time, although such data may alternatively be stored in the control unit 40.

If the total operational time 45 hits the threshold value, the control unit may either shut down, or may emit a warning advising the practitioner that the on-time limit has been reached. In some cases, the limit can be overridden by the practitioner. In other cases, reaching the limit disables the motor so that the device can no longer be used.

To the right of the four speed and time displays is a pump 46 that receives saline from an external IV bag and directs it into the handle 10 through the fluid supply line 17 (see FIG. 1). Once inside the handle 10, the saline is directed into the catheter 13, where it helps lubricate the drive shaft, cool the abrasive head, and flush away any debris.

It should be noted that in general, the saline from the fluid supply line 17 tends to leak a significant amount inside the handle. This leakage, although messy, is useful for lubricating and cooling the motor and the internal mechanisms of the handle, and is desirable. The leakage itself originates from slight gaps between concentric and overlapping tubes inside the handle, which form the seals. If these tubes are made to fit too snugly, the leakage may decrease, but the friction between the tubes and the rapidly rotating drive shaft may be prohibitively large. The tubes demonstrated for the electric motor device, shown and described herein, may leak only a fraction of earlier generation devices, but still leak a finite amount, and desirably so.

Saline travels from the IV bag, through a tube 61 to the pump 47, leaves the pump through an intermediate tube 62, passes through a void detector 48, and leaves the void detector 48 as the fluid supply line 17 (see FIG. 1).

The void detector 48 includes a light emitter, such as a light emitting diode, that shines light through the intermediate tube 62, and a photodetector diametrically across from the emitter that receives the light from the emitter. During normal operation, when the saline is flowing continuously through the intermediate tube without any bubbles, the light reaching the photodetector has a particular intensity that remains roughly constant. If the edge of a bubble passes by in the intermediate tube 62, the light reaching the photodetector is disrupted, and the photodetector output changes value. This change in value indicates that there is gas in the saline line (a "void"), and is used by the controller 40 to turn off the pump 47, in order to prevent the void from finding its way into the patient.

The button for "pump power" 51 toggles the power of the pump, from on to off, or from off to on. An LED or other indicator on or near the button may indicate if the pump is on.

The button for "prime" 52 turns on the pump, if the pump isn't already on, and sets the pump flow to a high rate, while the button is held down. The "prime" function flushes the pump system, and gets any air out of the system. The pump prime is typically used intermittently as needed.

The three buttons for "speed selection" are labeled "low", "medium" and "high", with an indicator light on each that corresponds to the selected speed. In general, for a particular model of handle 10 that is plugged into the control unit 40, there are preset speeds that are determined by the manufacturer. These speeds are automatically recognized by the control unit 40, so that the practitioner need not enter them manually. Such recognition may take place by, for instance, storage of the preset speeds on the handle 10, storage of the preset speeds in a lookup table on the control unit 40, and/or lookups-as-needed of the preset speeds through a central database, such as over the interne.

If the practitioner desires more fine control of the speed than is offered by the default low/medium/high presets, the increment buttons 54 may adjust the selected speed upward or downward by a predetermined increment, such as 10 kRPM, although any suitable increment may also be used.

The "IV bag reset" button 55 is used when a new IV bag is connected to the pump. In some cases, the user is prompted to enter the size of the IV bag. In other cases, a standard IV bag size is used. The controller 40 monitors the pump rate over time, and can effectively perform an integral of the pump rate, with respect to time, to calculate how much saline has been pumped out of the bag, and likewise, to calculate how much saline is left in the bag. When the amount of saline left in the bag drops below a predetermined threshold, the controller 40 may send a notification to the user by making a sound, flashing a light, or any other suitable notification.

Note that there is no manual control for the pump rate (or flow rate) of the pump 47. In general, the pump rate is determined at the factory, and is standardized for each rotation speed (low/medium/high), for each model of handle 10. This predetermined pump rate may be stored in a lookup table on the electronics embedded within the handle 10, may be stored in a lookup table on the electronics embedded with the control unit 40, may be calculated on the fly by the electronics in the control unit 40, may be looked up in real time from a central database, such as over the internet, or a combination of any of the above.

The "brake override" button 56 is typically used only when something gets stuck. During normal use, the guide wire remains extended from the handle, through the center of the drive shaft, past the abrasive element, and beyond the blockage. The drive shaft then rotates over the guide wire. During use, the guide wire remains rotationally stationary, and has a "brake" in the handle 10 that locks it rotationally and prohibits its rotation. Occasionally, there may be cases when something gets stuck, whether in the catheter itself, at the distal end of the drive shaft, or beyond the distal end of the drive shaft. When something gets stuck, the user may depress the "brake override" button 56, which allows the guide wire to rotate at a very low rotational speed. In some cases, the guide wire rotates at the same low rotational speed as the drive shaft. In other cases, the guide wire rotation is independent of the rotational speed of the drive shaft. Typically, the guide wire rotates as long as the brake override button 56 is held down.

Figure 5:
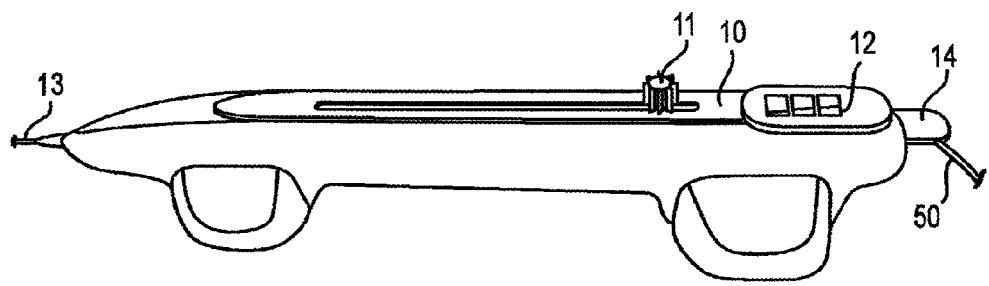
FIG. 5 is a plan drawing of the handle.

FIG. 5 is a plan drawing of a typical handle 10. The electrical connection 50 from the control unit 40 enters the handle 10 on the right side of FIG. 5. The catheter and drive shaft leave the handle 10 on the left side of FIG. 5. As with the controller, the layout of the controls is merely exemplary, and other suitable layouts may be used.

The control knob 11 longitudinally translates the drive shaft with respect to both the guide wire and the catheter, which remain stationary. The knob 11 slides along a channel with a travel range of about 15 cm. The control knob 11 is used extensively during the procedure, during which the practitioner positions and repositions the rapidly spinning abrasive head to fully remove the blockage in the blood vessel.

The control knob 11 may also include an optional on/off toggle button, which may turn on and off the electric motor in the handle.

The handle 10 may include a duplicate set of speed selection buttons 12, which can repeat the functionality of the corresponding buttons 53 on the controller. Having speed selection buttons 12 on the handle 10 itself is a great convenience for the practitioner.

Lever 14 is a brake for the guide wire, which, when engaged, prevents rotation of the guide wire as the drive shaft is rotated. In some cases, the guide wire brake 14 is locked when the lever is horizontal, as in FIG. 5, and is unlocked when pulled upward by the practitioner.

Figure 6:
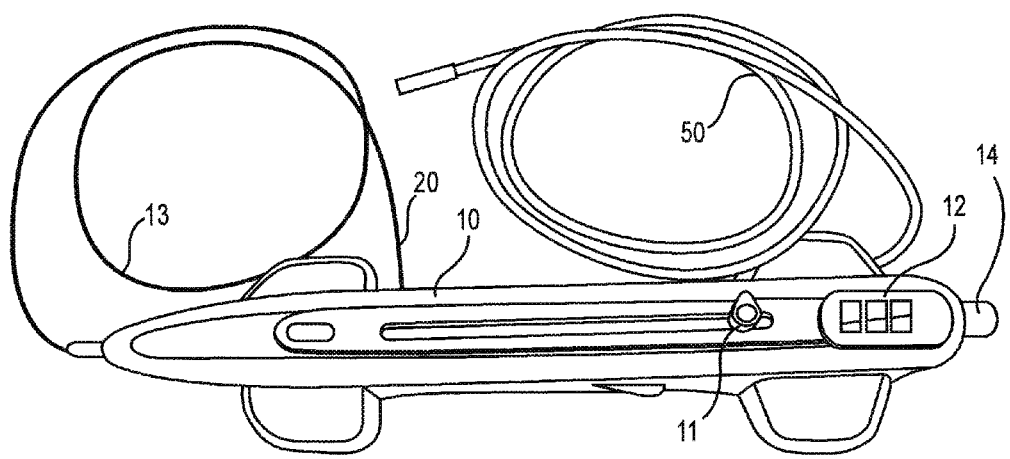
FIG. 6 is a top-view drawing of the handle of FIG. 5.

FIG. 6 is a top-view drawing of the handle 10 of FIG. 5. In addition to showing the control knob 11, the speed selection buttons 12 and the guide wire brake 14, FIG. 6 shows the electrical connection 50, which is typically a 14-foot-long cable although other suitable lengths may be used, and shows the catheter 13, typically connected to the body of the handle 10 with a strain relief The distal end of the drive shaft 20 is visible in FIG. 6, and is shown in more detail in FIG. 7.

Figure 7:
FIG. 7 is a top-view drawing of the distal end of the drive shaft, extending beyond the distal end of the catheter.

FIG. 7 is a top-view drawing of the distal end of the drive shaft 20, extending beyond the distal end of the catheter 13. The drive shaft 20 is typically a helically-wound coil of wire, although any suitable mechanism for delivering torque from the electric motor to the abrasive element 28 may be used as a drive shaft. For instance, an alternative drive shaft may be a solid or slotted tube of plastic or metal.

The abrasive element 28 shown in FIG. 7 is an enlarged portion of the drive shaft 20, with an abrasive material coated on the exterior of the enlarged portion. Alternatively, any suitable abrasive element may be used, including an element (a so-called "crown") having a center of mass that is laterally displaced from the rotation of the drive shaft (a so-called "eccentric" crown) and having an abrasive exterior. The eccentric solid crown is typically attached to the drive shaft, although it may alternatively be made integral with the drive shaft. The eccentric solid crown is typically attached near, but not at, the distal end of the drive shaft, although it may alternatively be attached at the distal end of the drive shaft.

Figure 8:
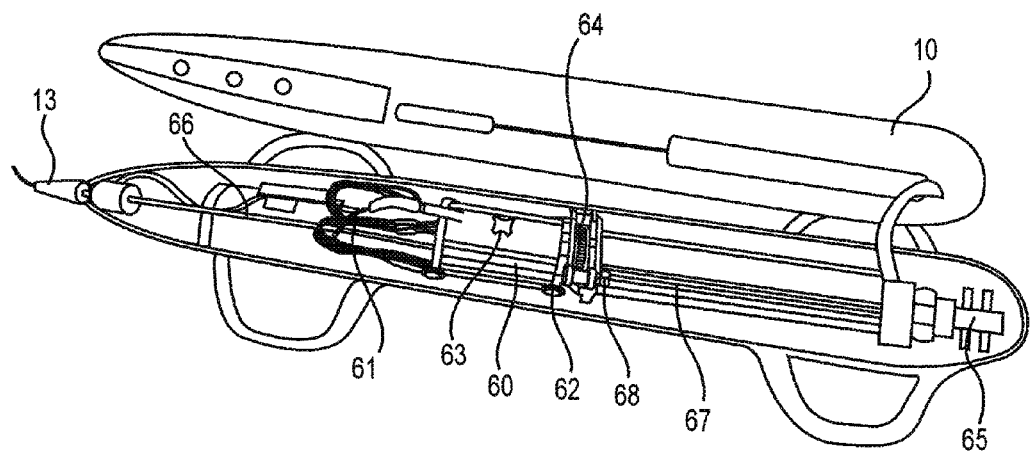
FIG. 8 is a top-view drawing of the handle of FIGS. 5 and 6, opened for clarity.
Figure 9:
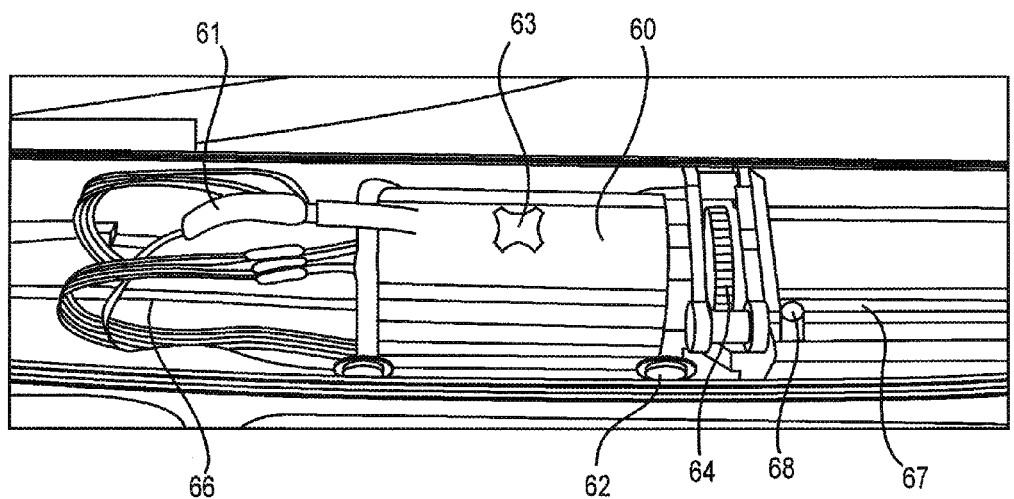
FIG. 9 is a close-up view of the carriage inside the handle of FIG. 8.

FIG. 8 is a top-view drawing of the handle 10, which is opened for clarity. FIG. 9 is a close-up view of the carriage inside the handle 10 of FIG. 8. In practice, the handle remains closed before, during and after the procedure. As with FIGS. 5 and 6, the catheter 13 and drive shaft 20 exit the left edge of the handle 10 in the view of FIG. 8.

The electric motor itself resides within a carriage 60. The exterior of the carriage 60 functions as a heat sink for the motor. The motor is powered by a series of electrical connections 61, which connect to the electrical connection 50 that in turn connects to the control unit 40.

The motor can travel longitudinally with a 15 cm range of travel, and does so being mounted on wheels 62 that engage respective tracks within the handle. Alternatively, other translating mechanism may be used. The handle is typically used for a single procedure and then disposed, so the wheels and tracks should be sturdy, but generally need not be designed for an especially long lifetime.

The carriage has an optional on/off toggle switch 63 on its top, which corresponds to the off/off button on the control knob 11. During use, the control knob 11 is directly above the toggle switch 63, and the practitioner may depress the knob 11 to turn the motor on and off.

There may be one or more gears 64 that step up or step down the rotation between the motor and the drive shaft. For instance, the motor itself may only have a maximum rotational speed of 50 kRPM, and a series of differently-sized gears may step the rotation up 4× to 200 kRPM for the drive shaft.

An advantage to having a geared system is that the guide wire may be routed through the center of a gear, rather than through the center of the motor. This simplifies the mechanical system.

Element 65 is another on/off switch, much like the toggle switch 63. One difference, however, is that the switch 65 is linked to the guide wire brake level 14. When the brake is released, the level is in the up position, and the switch 65 shuts off the motor, regardless of the state of any other on/off switches. When the brake is engaged, the switch 65 allows any other switch to toggle the motor on and off. There is accompanying circuitry for the switch 65, also located at or near the rightmost edge of the handle in FIG. 8.

Elements 66, 67 and 68 involve mechanical aspects of keeping the rapidly spinning drive shaft contained and stable, and of ensuring functional seals to keep fluids contained adequately. Elements 66 and 67 are telescoping mechanisms, such as concentric hypo tubes, which are tight enough to provide adequate fluid seals, and loose enough so that they do not rob the system of torque due to excessive friction.

As noted above, the interior of the handle 10 is not a perfectly dry system. The vapor and small amount of leaked liquid (saline) serves to cool the motor and the other moving parts in the handle and in the catheter. The front foot of the system (leftmost foot in FIG. 8) may be hollow and open, so that fluid can collect in it. The rear foot of the system (rightmost foot in FIG. 8) may include the CPU of the handle, which may be sealed between various foams and glues so that it doesn't get wet during use.

The motor and gears, spinning the drive shaft up to 200 kRPM, may produce significant vibrations inside the handle. In general, these vibrations are undesirable, and it is generally preferable to dampen these vibrations whenever possible. The telescoping portions, extending from the proximal edge of the handle to the carriage, and from the carriage to the distal edge of the handle, have their own resonant frequencies. The resonant frequencies of the portions can vary, depending on where in the range of travel the carriage actually is. As a result, completely avoiding a resonant frequency during use is generally difficult or impossible. One way to dampen the vibrations for a large range of resonant frequencies is to use one or more strain reliefs 68 within the coupling between carriage and telescopes.

Having described the mechanical structure of the electric motor and controller, we turn first to the unforeseen obstacles and then to the unforeseen advantages of replacing the known gas turbine with an electric motor.

The known gas turbines were generally small, plastic pieces that could be sped up to 200 kRPM using air pressure. The turbines themselves were generally small, easy to work with and had desirable mechanical characteristics, but the air-pressure-controlling systems that fed the turbines were expensive, cumbersome, and mechanically quite complicated. Swapping an old gas turbine out for an electrical motor presents some design and control challenges.

First, the rotational inertia of the electric motor can be up to 10 times larger than that of the tiny plastic gas turbine, or more. This presents serious challenges for the control system that controls the motor; simply using the old control system from the turbine will not work.

A typical control system for the gas turbine is as follows. A fiber optic at the turbine provides the actual rotational speed to the control system, which adjusts the pressure of the gas periodically to match the rotational speed to a desired speed. The control system can adjust the pressure up to a particular threshold value, such as 64 psi. If after a particular length of time, such as four seconds, the turbine is not spinning at its desired rotational speed, the control system assumes that something is impeding the rotation of the abrasive element, so the pressure is set to zero and the turbine stops. Similarly, if the fiber optic detects that the turbine is stopped, the control system assumes that the distal end of the drive shaft is caught up something, so the pressure is also set to zero.

It is instructive to examine the torques experienced by the abrasive element at the distal end of the drive shaft, when such a shutdown occurs. In particular, consider the case where the distal end of the drive shaft becomes caught on something, and it stops suddenly.

Initially, just after being caught, there is no torque at the abrasive element. From this zero value, the torque rises rapidly, since the turbine and the entire drive shaft are rotating, while the distal end of the tip remains stuck.

Eventually, the torque peaks, which occurs when the drive shaft is momentarily stationary. At this peak, all the angular momentum that was present in the previously-spinning drive shaft is converted into torque, by angularly compressing the drive shaft to its most compressed state.

Beyond this peak, the torque starts falling, as some of the angular compression pushes back on the turbine. During this stage, the distal end of the drive shaft remains stationary (because it's stuck), and the rest of the drive shaft, which extends back to its proximal end at the turbine, rotates in the opposite direction as the first stage described above.

Eventually, the angular compression is dissipated and the torque plateaus. At this plateau, the drive shaft is stationary throughout, but is angularly compressed in a steady-state by the angular force (torque) of the turbine. The plateau torque value is larger than zero, but smaller than the first peak described above. Using the control mechanism described above, the torque remains at this plateau value for about four seconds (minus the rise and settling time, which is typically in the range of milliseconds), and then the gas pressure to the turbine is shut off.

Figure 10:
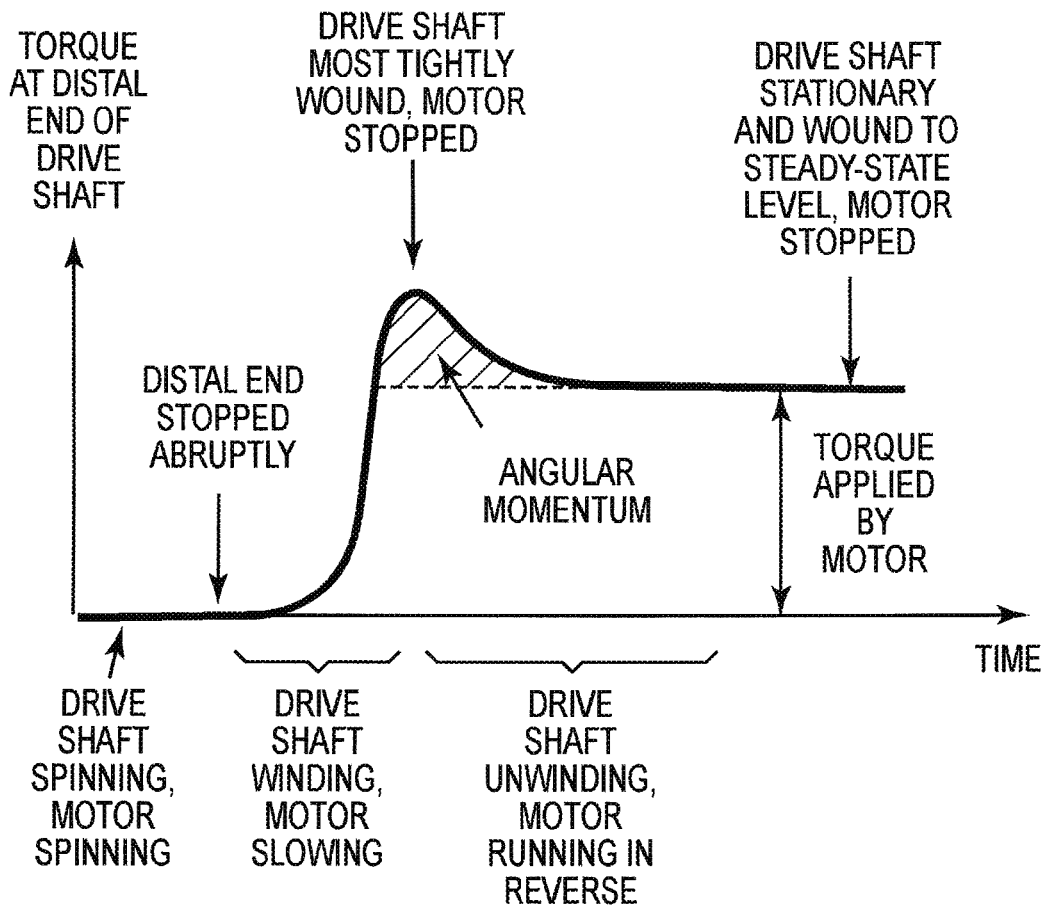
FIG. 10 is a plot of torque at the distal end of the drive shaft versus time for a distal end obstruction, for the gas turbine.

This is all shown in the plot of FIG. 10. The cross-hatched area under the large peak is the angular momentum of the motor, plus the angular momentum of the drive shaft and of any intervening components. For the known gas turbines, this value is acceptably small, and doesn't cause any problems. However, for the electric motors, the motor itself has much more angular momentum than any other components in the system, and this value can be much larger, by a factor of up to 10 or more. If the same control system were used with the electric motor, the large peak would be much larger, on the order of 10 times larger, if it scales with the angular momentum of the motor. This huge increase in torque would likely cause damage to the instrument, or worse, damage to the blood vessel in the patient. This is unacceptable.

One way to deal with the large angular momentum issue is to change the way the motor is handled once a blockage is detected. For the known gas turbines, it was adequate to wait four seconds, then cut off the gas pressure feeding the turbine. For the electric motor, however, there could be a great deal of damage in those four seconds.

Figure 11:
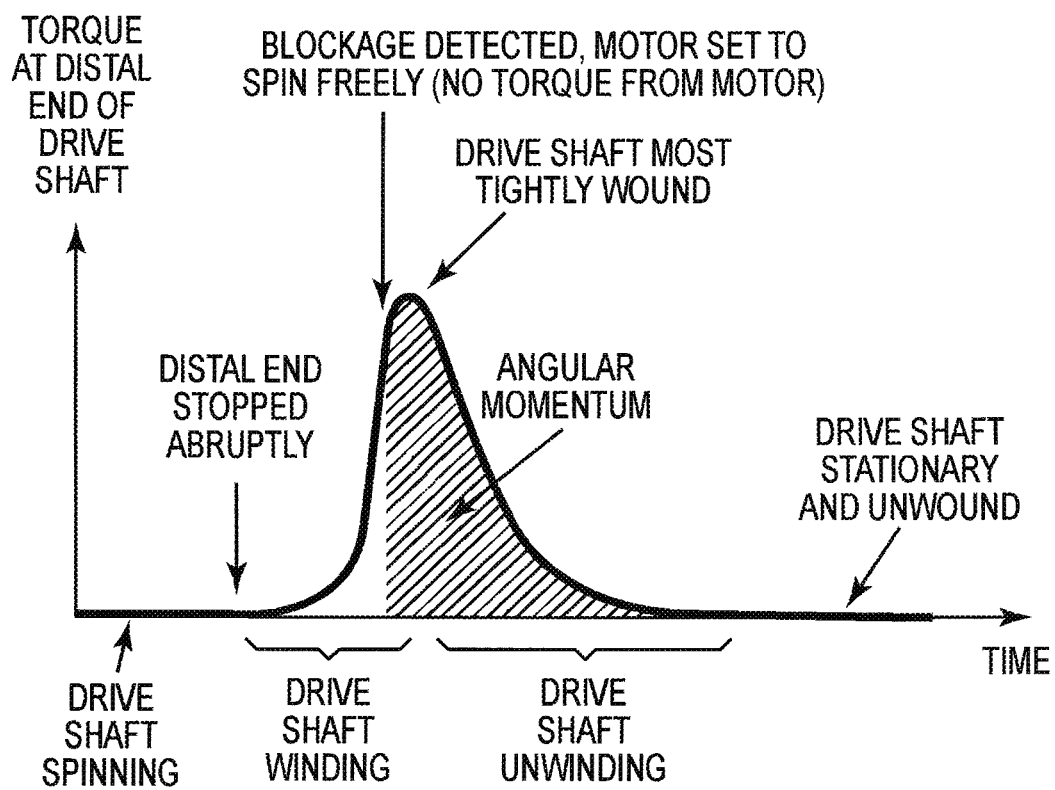
FIG. 11 is a plot of torque at the distal end of the drive shaft versus time for a distal end obstruction, for the electric motor.

One approach for quickly dissipating the angular momentum of the electric motor is shown schematically FIG. 11.

Initially, the device is working normally. The motor is applying a torque to the proximal end of the drive shaft, the drive shaft is spinning along with the motor, and the distal end of the drive shaft is spinning.

The device then encounters an obstruction that grabs the distal end of the drive shaft, causing it to stop rotating. On FIG. 11, this is the point labeled "distal end stopped abruptly".

The distal end of the drive shaft is stopped, but the motor continues to rotate the proximal end of the drive shaft. The drive shaft begins to wind up (compress rotationally), and the torque required to perform such winding gradually slows down the motor.

Once the motor rotation falls below a particular threshold, which can be a fixed value below the desired rotation speed and/or a percentage drop from the desired rotation, the control unit decides that an obstruction has been detected. The control unit responds by releasing the motor and allowing it to spin freely as a flywheel. On FIG. 11, this occurs at the point labeled "blockage detected, motor set to spin freely (no torque from motor)".

The drive shaft continues to wind up (compress rotationally), under the influence of the angular momentum of the free-spinning motor. At some point, all the rotational kinetic energy from the angular momentum is converted to rotational potential energy, and the drive shaft reaches its most tightly wound point.

The drive shaft then unwinds, converting essentially all of its rotational potential energy into rotational kinetic energy and spinning the free-spinning motor in the opposite direction. On FIG. 11, this occurs in the region labeled "drive shaft unwinding".

Note that there are likely some oscillations in this portion, where the curve oscillates about zero with decreasing amplitude over time (damped oscillations). Eventually, the curve settles to a steady-state at zero, where the drive shaft is essentially unwound and stationary, the motor is essentially stationary, and there is no torque applied to the end of the distal end of the drive shaft. This is a relaxed, steady-state condition, where all of the kinetic and potential energy has been dissipated through friction and other losses.

Note that the horizontal time axis of FIG. 11 is not necessarily the same as that in FIG. 10. In practice, the settling time of FIG. 11 is on the order of milliseconds.

There are two quantities of note in FIG. 11.

First, the peak value of the solid curve is the maximum torque that is applied at the distal end of the drive shaft. If this maximum torque exceeds a particular value, there may be damage to the instrument, or worse, damage to the blood vessel of the patient. It was found in practice that the peak value for the gas turbine, shown schematically in FIG. 10, was low enough so that it didn't cause any damage. For the electric motor, shown in FIG. 11, the control algorithm attempts to keep the peak torque value at or below that shown in FIG. 10 for the gas turbine, with the logic that if that torque value didn't cause any problems for the turbine, it shouldn't cause any problems for the electric motor either.

Second, the cross-hatched region represents the angular momentum of the electric motor, the drive shaft and the accompanying coupling elements. In practice, the electric motor completely overshadows the other contributions. This "area under the curve" is essentially a fixed quantity for a particular motor and rotation speed, and it is the job of the control algorithm to "smooth" that area out along the horizontal axis, while ensuring that the peak torque doesn't exceed a particular value. The challenge of the electric motor is that the cross-hatched area is significantly larger than for the gas turbine, by a factor of up to 10 or more.

Once the hurdle of dealing with the increased angular momentum is cleared, there are many advantages to having an electric motor, rather than a gas-fed turbine.

For instance, one advantage is that various quantities may be stored in the electronic memory of the control unit 40 and/or the handle 10, such as low/medium/high preset rotation speeds for a particular model of handle, maximum and/or minimum rotation speeds of the electric motor (i.e. threshold values, beyond which the device causes damage or becomes ineffective), maximum and/or minimum current supplied to the electric motor (more thresholds), maximum and/or minimum torque delivered by the electric motor (yet more thresholds), performance specifications (such as the cumulative maximum time of operation for a particular handle), and IV bag quantities (bag size, preferred pump rate as a function of rotational speed, amount of fluid left in bag).

Compared with the known gas turbines, there are many additional quantities now available, such as preferred pump rate as a function of rotational speed. As a result, the electric motor provides a great deal of new, additional functionality, such as automatically adjusting the pump rate to the preferred level when the rotational speed of the motor is changed. Another example of new functionality is the "brake override" feature, described in detail above, which would be completely unavailable on a gas turbine-driven system. This additional functionality is an unexpected result of merely using an electric motor, rather than the known gas turbine.

Another advantage is that the control unit 40 for the electric motor is simpler, less cumbersome and less expensive than the unit that controls the gas pressure fed to a gas turbine. In addition, the device with an electric motor can be used without a high-pressure air line nearby.

The rotational speed, current being fed to the motor and voltage applied to the motor may all vary over the course of a procedure, and may all be used to detect particular milestones in the procedure. For instance, in the initial portion of a procedure, as a hard part of the blockage puts up a lot of resistance as it is scraped away, the motor requires a relatively large amount of current to begin the abrading. This initial portion has a relatively large current, matched with a relatively low rotational speed. As the procedure progresses and some of the blockage has been scraped or sanded away, the motor requires less current to do the abrading. At this stage, the current has dropped and the motor rotational speed remains essentially the same or has increased. If the tip of the atherectomy head becomes stuck in a blockage, the rotational speed drops rapidly and the current rises rapidly. In general, changes in at least one of the rotational speed, the motor current and the motor voltage may be used to detect particular milestones in the procedure.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. A rotational atherectomy system, comprising:
   an elongated, flexible drive shaft having a distal end for insertion into a vasculature of a patient and having a proximal end opposite the distal end remaining outside the vasculature of the patient;
   an abrasive element on the drive shaft proximate the distal end of the drive shaft;
   an electric motor coupled to the proximal end of the drive shaft; and
   control electronics for:
      supplying electrical power to the motor for rotating the motor in a first direction and applying an electrical-power-induced torque at the proximal end of the drive shaft whereby the drive shaft is rotated in the first direction; and
      monitoring a rotational speed of the motor in the first direction;
   wherein,
      when the distal end of the drive shaft encounters an obstruction and stops rotating, the control electronics continue to supply electrical power to the motor for continuing the rotation of the motor in the first direction and continuing the application of the electrical-power-induced torque at the proximal end of the drive shaft whereby the drive shaft begins to wind up and decreases the rotational speed of the motor;
      when the rotational speed of the motor in the first direction decreases below a threshold, the control electronics releases the motor by interrupting the electrical power supplied to the motor whereby:
         no electrical-power-induced torque is applied at the proximal end of the drive shaft;
         the motor is enabled to spin freely as a fly wheel; and
         only a rotational kinetic energy from an angular momentum of the just released free-spinning motor applies a kinetic-energy-induced torque at the proximal end of the drive shaft such that the drive shaft continues to rotate in the first direction under the influence of the kinetic-energy-induced torque until the rotational kinetic energy is converted to a rotational potential energy and the drive shaft reaches its most tightly wound point and stops rotating in the first direction;
      when the drive shaft is most tightly wound, the rotational potential energy is converted into rotational kinetic energy whereby the kinetic-energy-induced torque rotates the drive shaft and the released free-spinning motor in a second direction opposite the first direction until the drive shaft unwinds and stops rotating in the absence of any torque being applied at its proximal end; and
      the drive shaft and abrasive element, when rotating, have a torque limited by a current supplied to the electric motor.

2. The rotational atherectomy system of claim 1,
   wherein the electric motor is contained within a handle; and
   wherein the control electronics are contained in a control unit separate from the handle and electrically tethered to the handle.

3. The rotational atherectomy system of claim 2, wherein the control unit includes internal memory for storing performance specifications.

4. The rotational atherectomy system of claim 2, wherein the control unit includes an external activation control and an external electric motor rotational speed control.

5. The rotational atherectomy system of claim 2, wherein the control unit is simultaneously operable with an electronic heart defibrillator.

6. The rotational atherectomy system of claim 2, wherein the control unit includes a void detector that ensures reliable delivery of saline to the vasculature of the patient.

7. The rotational atherectomy system of claim 1,
   wherein the abrasive element has a center of mass that is laterally displaced from a rotational axis of the drive shaft; and
   wherein the abrasive element includes an abrasive exterior surface.

8. The rotational atherectomy system of claim 1, wherein the abrasive element comprises an eccentric solid crown attached to the drive shaft.

9. A rotational atherectomy system, comprising:
   an elongated, flexible drive shaft having a distal end for insertion into a vasculature of a patient and having a proximal end opposite the distal end remaining outside the vasculature of the patient;
   an eccentric solid crown on the drive shaft proximate the distal end of the drive shaft;
   an electric motor coupled to the proximal end of the drive shaft; and
   control electronics for:
      supplying electrical power to the motor for rotating the motor in a first direction and applying an electrical-power-induced torque at the proximal end of the drive shaft whereby the drive shaft is rotated in the first direction; and
      monitoring a rotational speed of the motor in the first direction;
   wherein,
      when the distal end of the drive shaft encounters an obstruction and stops rotating, the control electronics continue to supply electrical power to the motor for continuing the rotation of the motor in the first direction and continuing the application of the electrical-power-induced torque at the proximal end of the drive shaft whereby the drive shaft begins to wind up and decreases the rotational speed of the motor;
      when the rotational speed of the motor in the first direction decreases below a threshold, the control electronics releases the motor by interrupting the electrical power supplied to the motor whereby:
         no electrical-power-induced torque is applied at the proximal end of the drive shaft;
         the motor is enabled to spin freely as a fly wheel; and
         only a rotational kinetic energy from an angular momentum of the just released free-spinning motor applies a kinetic-energy-induced torque at the proximal end of the drive shaft such that the drive shaft continues to rotate in the first direction under the influence of the kinetic-energy-induced torque until the rotational kinetic energy is converted to a rotational potential energy and the drive shaft reaches its most tightly wound point and stops rotating in the first direction;
      when the drive shaft is most tightly wound, the rotational potential energy is converted into rotational kinetic energy whereby the kinetic-energy-induced torque rotates the drive shaft and the released free-spinning motor in a second direction opposite the first direction until the drive shaft unwinds and stops rotating in the absence of any torque being applied at its proximal end; and the control unit includes a void detector that ensures reliable delivery of saline to the vasculature of the patient.

10. The rotational atherectomy system of claim 9, wherein the eccentric solid crown has a center of mass that is laterally displaced from a rotational axis of the drive shaft; and wherein the eccentric solid crown includes an abrasive exterior surface.

* * * * *